United States Patent
Rausch et al.

(10) Patent No.: US 6,355,747 B1
(45) Date of Patent: Mar. 12, 2002

(54) ASYMMETRIC SILICON-BRIDGED METALLOCENES USEFUL AS CATALYSTS IN THE POLYMERIZATION OF α-OLEFINS, PROCESS FOR THEIR PREPARATION AND USE OF SAID METALLOCENES FOR THE POLYMERIZATION OF α-OLEFINS

(75) Inventors: Marvin D. Rausch; Emma J. Thomas, both of Amherst, MA (US); Serge Bettonville, Crisnée; Fabian Siberdt, Brussels, both of (BE)

(73) Assignee: Solvay Polyolefins Europe-Belgium, Brussels (BE)

( * ) Notice: Subject to any disclaimer, the term of this patent is extended or adjusted under 35 U.S.C. 154(b) by 0 days.

(21) Appl. No.: 09/376,179

(22) Filed: Aug. 17, 1999

(51) Int. Cl.[7] .................................................. C08F 4/42
(52) U.S. Cl. ..................... 526/160; 526/348; 526/351; 526/126; 526/943; 502/152
(58) Field of Search ................................ 526/160, 943, 526/348, 126, 351; 502/152

(56) References Cited

U.S. PATENT DOCUMENTS 5,770,664 A * 6/1998 Okumura et al. ........... 526/127

FOREIGN PATENT DOCUMENTS

| EP | 707 016 A1 | 4/1996 |
|---|---|---|
| EP | 754 698 A2 | 1/1997 |
| JP | 10 204112 A | 8/1998 |

OTHER PUBLICATIONS

Thomas, E.J. et al., "Influence of Alkyl Substituents on the Polymerization Behaviour of Asymmetric Ethylene–bridged Zirconocene Catalysts," Organometallics, vol. 18, pp. 1439–1443 (1999).

You–Xiun, C. et al., "Silylene–bridged Fluyorenyl–containing Ligands and Zirconium Complexes with C1 and Cs Symmetry: General Synthesis and Olefin Polymerization Catalysis," Journal of Organometallic Chemistry, vol. 497, pp. 1–9 (1995).

EPO Search Report of Dec. 5, 2000.

Spaleck, et al. The Influence of Aromatic Substituents on the Polymerization Behaviour of Bridge Zirconene Catalysts, Organmetallics 1994, vol. 13, pp. 954–963.

* cited by examiner

*Primary Examiner*—David W. Wu
*Assistant Examiner*—Ling-Siu Choi
(74) *Attorney, Agent, or Firm*—Venable; Marina V. Schneller

(57) ABSTRACT

Asymmetric silicon-bridged metallocenes represented by the general formula:

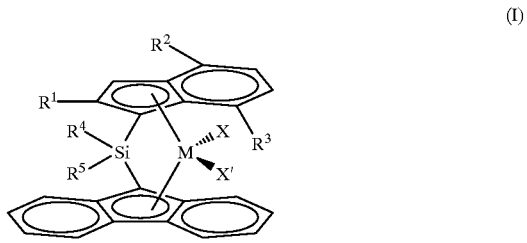

(I)

wherein
M represents a transition metal selected from Ti, Zr and Hf.
X and X' represent a halogen atom,
$R^1, R^2, R^3$ represent alkyl groups containing 1 or 2 carbon atoms or hydrogen atoms, providing that at least two of $R^1, R^2, R^3$ are alkyl groups, and
$R^4$ and $R^5$ represent alkyl or aryl group containing from 1 to 10 carbon atoms. A process for their preparation and polymerization of olefins in the presence of the asymmetric silicon-bridged metallocenes are disclosed.

5 Claims, No Drawings

ASYMMETRIC SILICON-BRIDGED METALLOCENES USEFUL AS CATALYSTS IN THE POLYMERIZATION OF α-OLEFINS, PROCESS FOR THEIR PREPARATION AND USE OF SAID METALLOCENES FOR THE POLYMERIZATION OF α-OLEFINS

TECHNICAL FIELD

The present invention relates to novel asymmetric silicon-bridged metallocenes useful as catalysts for the polymerization of α-olefins. It relates more specifically to novel silicon-bridged metallocenes containing fluorenyl and indenyl fragments and to a process for their preparation. Finally it relates to a process for polymerization of α-olefins by using said asymmetric silicon-bridged metallocenes.

BACKGROUND OF THE INVENTION

Some asymmetric silicon-bridged metallocenes derived from group 4 metals and containing fluorenyl and indenyl fragments have already been proposed for the polymerization of α-olefins such as ethylene and propylene. For example, EP-A-0 754 698 discloses specifically dimethyl- or diphenyl-silylene (9-fluorenyl)-(2-methyl-1-indenyl) zirconium dichloride, dimethylsilylene (9-fluorenyl)-(2-methyl-4-phenyl-1-indenyl)zirconium dichloride, dimethylsilylene (9-fluorenyl)-(3-methyl-1-indenyl)zirconium dichloride and dimethylsilylene (9-fluorenyl)-(2-methyl-4-i-propyl-7-methyl-1-indenyl)zirconium dichloride in combination with aluminoxanes (MAO) for the polymerization of these α-olefins. However the productivity of such silicon-bridged metallocenes remains insufficient and they do not lead to polymers having optimal properties.

Silicon-bridged indenyl fluorenyl metallocenes are generally produced by processes involving the addition of the indenyl anion to the (9-fluorenyl) silylhalide (J. Organomet. Chem., 1995, 497, 1). The application of this known route to substituted indenyl compounds does not provide satisfactory results presumably due to unfavorable steric hindrance of the indenyl compound.

SUMMARY OF THE INVENTION

It is an object of the present invention to solve the above problems by providing novel metallocenes useful as catalysts for olefin polymerization which are, in particular, able to produce with a particularly high activity polyethylene having high molecular weight. It is another objective of the present invention to provide a process for preparing said novel metallocenes and to provide a process for polymerization of the α-olefins by means of said metallocenes.

The invention is thus related to novel metallocenes represented by the general formula (I)

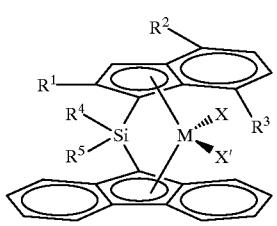

(I)

wherein

M represents a transition metal selected from Ti, Zr and Hf,

X and X' represent a halogen atom, $R^1$, $R^2$, $R^3$ represent an alkyl group containing 1 or 2 carbon atoms or a hydrogen atom, providing that at least two of $R^1$, $R^2$, $R^3$ are alkyl groups, and $R^4$ and $R^5$ represent an alkyl or aryl group containing from 1 to 10 carbon atoms.

The invention also relates to a process for the preparation of metallocenes represented by the general formula (I) comprising the following steps:

a) production of (substituted indenyl)-alkyl(or aryl)-chlorosilane starting from (substituted indenyl)lithium and dichloro-dialkyl(or diaryl)silane, b) production of (9-fluorenyl)-1-(substituted indenyl)-dialkyl(or diaryl)silane from the compound obtained in step (a) and fluorenyllithium, c) production of the dilithium salt of (9-fluorenyl) (1-substituted indenyl)-dialkyl(or diaryl)silane precursor and d) production of the metallocene by reacting the said dilithium salt with a halide of one of the transition metals mentioned hereabove.

Finally the present invention relates to a process for polymerization of α-olefins by means of said metallocenes.

DETAILED DESCRIPTION

According to a first aspect, the present invention relates to novel metallocenes of the above general formula (I).

Preferably the transition metal is selected from hafnium and zirconium. Most preferably the transition metal is zirconium.

The halogen atoms X and X' are preferably chlorine or bromine atoms and most preferably they are both chlorine atoms.

The groups $R^1$, $R^2$, $R^3$ represent preferably a methyl group or a hydrogen atom, providing that at least two of $R^1$, $R^2$, $R^3$ are methyl groups.

The groups $R^4$ and $R^5$ are preferably alkyl groups and more particularly alkyl groups containing from 1 to 3 carbon atoms.

The most preferred metallocenes according to the present invention are dimethylsilylene (9-fluorenyl)-1-(2,4,7-trimethyl)indenyl zirconium dichloride, dimethylsilylene (9-fluorenyl)-1-(2,4-dimethyl)indenyl zirconium dichloride or dimethylsilylene (9-fluorenyl)-1-(4,7-dimethyl)indenyl zirconium dichloride.

When used in combination with a cocatalyst, such as for example aluminoxane, said novel metallocenes are able to produce polypropylene and more particularly polyethylene with high molecular weight.

According to a second aspect, the present invention relates to a process for producing the novel metallocenes of general formula (I).

The said process comprises the following steps:

a) reacting dichloro-dialkyl(or diaryl)silane with (substituted indenyl)lithium to produce (substituted indenyl)-dialkyl(or diaryl)-chlorosilane, b) reacting said chlorosilane with fluorenyllithium to produce the (9-fluorenyl)-1-(substituted indenyl)-dialkyl(or diaryl)-silane precursor, c) reacting said (9-fluorenyl)-1-(substituted indenyl)-dialkyl(or diaryl)-silane precursor with butyllithium to produce its dilithium salt, and d) reacting said dilithium salt with a transition metal halide selected from halides of Ti, Zr and Hf to produce the metallocenes.

Preferably, step (a) is carried out with an excess of the chlorosilane. More preferably the (substituted indenyl) lithium is reacted with about two molar equivalents of the silane.

Preferably, step (b) is carried out by reacting the fluorenyllithium with the chlorosilane in equimolar quantity.

Preferably, step (c) is carried with at least two molar equivalents of butyllithium per mole of the (9-fluorenyl)-1-(substituted indenyl)-dialkyl(or diaryl)-silane precursor. Step (d) is most often carried out by reacting the dilithium salt with one equivalent of transition metal halide.

Preferably, reaction step (a) is carried out in an inert solvent, for example an ether. Reaction step (a) is usually carried out at a temperature in the range of about 0° C. to about room temperature. At the end of reaction of step (a), the solvent and the excess of dichloro-dialkyl(or aryl)-silane are generally removed in order to separate the produced substituted indenyl-alkyl(or aryl)-chlorosilanes which are oils.

Preferably, the step (b) is carried out in the above-mentioned inert solvent, most often about room temperature. At the end of reaction, the suspension is usually hydrolyzed and the organic phase is isolated. After removal of the solvent, the (9-fluorenyl)-1-(substituted indenyl)-dialkyl(or diaryl)-silane precursor is isolated.

Preferably, step (c) is carried out in an inert solvent, such as toluene or an ether, often under the reflux of said solvent. The resulting Li salt is advantageously separated from the solvent and washed prior to being reacted, in step (d), with about one equivalent of a transition metal halide selected from halides of Ti, Zr and Hf.

Step (d) is preferably carried out in an inert solvent, such as toluene or an ether, often under the reflux of said solvent. After removal of the solvent, the solid metallocene is isolated.

The novel metallocenes according to the present invention are useful as catalysts for the polymerization of α-olefins. The reaction is carried out by contacting said α-olefins with the said metallocene under polymerization conditions. It can be carried out in solution or in suspension in an hydrocarbon diluent or in suspension in one of the monomers maintained in the liquid form or in the gas phase. The polymerization conditions are well known by persons skilled in the art.

The metallocenes according to the invention can be used in combination with one another. They can also be used in combination with aluminoxanes. Methylaluminoxane is preferred. They can also be used in combination with an ionizing agent. This ionizing agent can be chosen from the compounds comprising a first part which has the properties of a Lewis acid and which is capable of ionizing the metallocene and a second part that is inert towards the ionized metallocene. Examples of ionizing agents are triphenylcarbenium tetrakis(pentafluorophenyl)borate, N,N'-dimethylanilinium tetrakis(pentafluorophenyl)borate, tri(n-butyl)ammonium tetrakis(pentafluorophenyl)borate, tri (pentafluorophenyl)boron, triphenylboron,trimethylboron, tri(trimethylsilyl)borate and organoboroxines.

Organometallic compounds are generally used as cocatalysts and/or poison scavengers. They can be selected from organometallic compounds of lithium, magnesium, zinc, aluminium or tin. The best results are obtained with organoaluminium compounds and in particular with trialkylaluminium compounds.

The olefins can be chosen from those containing up to 20, preferably up to 12 carbon atoms per molecule. The olefin is preferably ethylene or propylene. The metallocenes according to the present invention may be used for the homopolymerization of one of these olefins or for the copolymerization—random or block copolymerization—of one of these olefins with one or more comonomers. The preferred comonomers of ethylene are butene, hexene and their mixtures. The preferred comonomers of propylene are ethylene, butene and their mixtures.

The novel metallocenes according to the invention are especially well adapted to the polymerization of ethylene in order to produce with a particularly high activity a polyethylene having high molecular weight. The metallocenes according to the invention are furthermore well suited for obtaining linear polyethylene, i.e. polyethylene whose NMR $^{13}C$ spectra shows substantially no branching. Polyethylenes having high melting point are advantageously obtained.

In addition to the foregoing description of the invention, the following examples are provided to illustrate the present invention.

In these examples reactions are carried out under an argon atmosphere using standard Schlenk, techniques. Toluene, diethyl ether, tetrahydrofuran (THF) and pentane were distilled from Na/K alloy under argon. Dichloromethane was distilled from $CaH_2$ under argon.

Melting points of the polymers were determined by DSC with a Perkin-Elmer DSC-System. $^{13}C$ NMR spectra were determined on DPX300/AMX500 spectrometers in $CDCl_3$ at room temperature, and at 80° C. in $C_6D_5Cl$. $^1H$ NMR spectra were recorded on a AC-200 spectrometer.

1. Preparation of Metallocenes

EXAMPLE 1

Preparation of the dimethylsilylene (9-fluorenyl)1-(2,4,7-trimethyl)indenyl zirconium dichloride a) Production of (2,4,7-trimethyl)indenyl-dimethylsilane To a solution of 5.00 g (31.6 mmol) of (2,4,7-trimethyl) indene in 30 ml of dry diethyl ether and 10 ml of dry THF at 0° C., was added dropwise a 1.6 M solution of butyllithium in hexane (19.70 ml, 31.6 mmol). The solution was stirred at room temperature for 5 h and then added dropwise via cannula to 7.67 ml (63.2 mmol) dichloro-dimethylsilane in 20 ml of dry diethyl ether at 20° C. The addition was carried out over a 1 h period and the suspension was then stirred for 1 h at room temperature. The solvents and excess dichloro-dimethylsilane were then removed under vacuum.

b) Production of (9-fluorenyl)-1-(2,4,7-trimethyl)indenyl-dimethylsilane

The oil obtained in step (a) was suspended in 30 ml of dry diethyl ether at 0° C. To this was added dropwise by cannula one equivalent of fluorenyllithium prepared from 5.25 g (31.6 mmol) of fluorene and 19.7 ml (31.6 mmol) of butyllithium in 30 ml of dry ether and 10 ml of dry tetrahydrofuran. The suspension was allowed to stir overnight at room temperature and hydrolyzed with aqueous $NH_4Cl$. The organic phase was separated and the aqueous layer was extracted with ether. The combined organic phases were dried ($MgSO_4$), filtered and the solvent was removed. The residue was recrystallized from toluene/hexane 1:1 to give 9.05 g of (9-fluorenyl)-1-(2,4,7-trimethyl)indenyl-dimethylsilane (75%); melting point 121–123° C. $^1H$ NMR ($CDCl_3$): δ7.90–7.34 (m, 8H, arom), 6.95–6.88 (d, 1H), 6.78–6.75 (d, 1H), 6.66–6.65 (d, 1H), 4.17, (s, 1H, Flu $sp^2$), 3.85 (s, 1H, Ind $sp^2$), 2.38 (s, 3H, $CH_3$), 2.27 (s, 3H, $CH_3$), 2.11 (s, 3H, $CH_3$), −0.32 (s 3H, Si—$CH_3$), −0.55 (s 3H, Si—$CH_3$). Anal. Calcd for $C_{27}H_{28}Si$: C, 85.21; H, 7.41. Found: C, 85.47; H, 7.35.

c) Production of the Dilithium Salt

To a solution of 1.00 g (2.63 mmol) of (9-fluorenyl)-1-(2,4,7-trimethyl)indenyl-dimethylsilane in 20 ml of dry toluene at 0° C. was added dropwise two equivalents of a 1.6 M solution of butyllithium in hexane (3.3 ml, 5.25 mmol). The solution was heated under reflux for 5 h giving an orange suspension.

d) Production of dimethylsilylene (9-fluorenyl)-1-(2,4,7-trimethyl)indenyl zirconium dichloride The suspension obtained in (c) was cooled to −25° C. and zirconium tetrachloride (0.61 g, 2.63 mmol) was added as a solid. After stirring at room temperature overnight, the mixture was heated under reflux for an additional 4 h to ensure complete reaction. Upon cooling to room temperature, the suspension was filtered and the orange residue was extracted with dry methylene chloride.

The solution was concentrated and stored at −20° C. to give 156 mg of dimethylsilylene-(9-fluorenyl)-1-(2,4,7-trimethyl)indenyl zirconium dichloride as an orange powder (11%). $^1$H NMR (CDCl$_3$): δ8.00–6.62 (m, 11H, arom), 2.72 (s, 3H, CH$_3$), 2.38 (s, 3H, CH$_3$), 2.23 (s, 3H, CH3), 1.47–1.46 (d, 6H, Si—CH$_3$). Anal. Calcd for $C_{27}H_{26}SiCl_2Zr.0.08C_{27}H_{28}Si$: C,61.32; H, 4.98. Found: C, 61.80; H, 5.00.

EXAMPLE 2

Preparation of dimethylsilylene (9-fluorenyl-1-(2,4-dimethyl)indenyl zirconium dichloride Following the procedure of steps a) to d) of example 1, using diethyl ether at room temperature as the solvent in steps c) and d), dimethylsilylene(9-fluorenyl)-1-(2,4-dimethyl)indenyl zirconium dichloride (225 mg, 15.6%) was prepared using 2,4-dimethyl)indenyl lithium in stead of 2,4,7-trimethylindenyl lithium in step a). It is an orange solid. $^1$H NMR (CDCl$_3$):δ7.76–6.73 (m, 11H, arom), 6.62 (s, 1H, Ind-C$_5$), 2.28 (s, 3H, CH$_3$), 2.26 (s, 3H, CH$_3$), 1.54–1.43 (d, 6H, Si—CH$_3$). Anal Calcd; for $C_{26}H_{24}Cl_2SiZr.0.3CH_2Cl_2$:C, 57.21; H, 4.49. Found; C; 57.28; H,4.30

2. Polymerization of Olefins
General Conditions

A 250 ml crown capped glass pressure reactor containing 50 ml of toluene was equilibrated with the appropriate monomer and pressure at the desired temperature. The desired amount of methylaluminoxane (MAO) was added and the solution was stirred for 5 min. 1 ml of the appropriate metallocene catalyst solution in toluene, in precontact with 1 ml MAO, was added and the mixture was stirred until the desired reaction time was reached. The mixture was quenched with 2% HCl in methanol, filtered and dried in a vacuum oven at an appropriate temperature for the polymer sample.

EXAMPLES 3 and 4

These examples are related to the polymerization of propylene under the general conditions described hereabove by using the dimethylsilylene (9-fluorenyl)-1-(2,4,7-trimethyl)indenyl zirconium dichloride. The conditions are as follows:

Zr=25 μM
Al/Zr=4000:1 (molar ratio)
pressure=30 psi

The duration of the polymerization was 60 min, the temperature was 20° C. for example 3 and 70° C. for example 4. The yield was 1.8 g for example 3 (activity: 0.14×10$^7$ g polymer/(mol Zr.[propylene].h) and 0.4 g for example 4 (activity: 0.23×10$^7$ g polymer/(mol Zr. [propylene].h), the melting point was 74° C. for example 4 and 125° C. for example 5.

EXAMPLE 5

This example is related to the polymerization of ethylene according to the general conditions disclosed hereabove by means of dimethylsilylene-(9-fluorenyl)-1-(2,4,7-trimethyl) indenyl zirconium dichloride.

The conditions are as follows:

Zr=5 μM
Al/Zr=4000/1

The duration of the polymerization was 10 min, the temperature was 50° C. The yield was 0.61 g (activity: 5.3×10$^7$ g polymer/(mol Zr.[ethylene].h).

The polyethylene was characterized by a molecular weight (Mw) of 375931, a polydispersity (Mw/Mn) of 3.1, a melting point of 134.7° C. and a melting enthalpy of 158.5 J/g.

EXAMPLE 6

This example is related to propylene bulk polymerization with the dimethylsilylene (9-fluorenyl)-1-(2,4,7-trimethyl) indenyl zirconium dichloride according to the following general procedure: the polymerization run is carried out in a 5 liters stainless steel reactor. Cocatalyst (MAO, 10% by weight in toluene, 45 ml), catalyst (5 μmol Zr in precontact with 5 ml MAO, 10% by weight in toluene), Al/Zr=15,000:1 (molar ratio), and liquid propylene (3.5 liters) are successively introduced under argon blanket and heated to the polymerization temperature (70° C.). The polymerization conditions are maintained for 60 minutes. The polymerization is then stopped by simultaneously flashing the residual monomer and cooling down the reactor.

The results of polymerization were the following: activity: 0.074 10$^8$ g polypropylene/mol Zr, melting temperature: 95.7° C. Isotacticity [mmmm] measured by $^{13}$C NMR: 79 mol %, Mw 43,000.

EXAMPLE 7

This example is related to ethylene polymerization in liquid isobutane with the dimethylsilylene (9-fluorenyl)-1-(2,4dimethyl)indenyl zirconium dichloride. The polymerization run is carried out in a 3 liters stainless steel reactor. Cocatalyst (MAO, 10% by weight in toluene, 5 ml) and 1 liter liquid isobutane are successively introduced under nitrogen blanket and heated to 70° C. Ethylene is then introduced under an over pressure of 10 bars followed by catalyst (1 μmol Zr in precontact with 5 ml MAO (10% by weight in toluene).

These polymerization conditions are maintained for 20 minutes. The polymerization is then stopped by simultaneously venting and cooling down the reactor.

The results were:

activity: 1000 g polyethylene/mmol Zr, Mw=497 000.
What is claimed is:
1. Novel asymmetric silicon-bridged metallocenes used as catalyst components in the polymerization of propylene to produce isotactic polypropylene represented by the general formula (I)

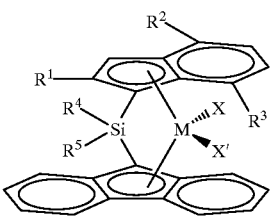

(I)

wherein

M represents Zr,

X and $X^1$ are chlorine, $R^1$, $R^2$, $R^3$ represent methyl groups or hydrogen atoms, providing that at least two of $R^1$, $R^2$, $R^3$ are methyl groups, and $R^4$ and $R^5$ represent alkyl groups containing from 1 to 3 carbon atoms.

2. A novel asymmetric silicon-bridged metallocene according to claim 1, which is dimethylsilylene (9-fluorenyl)-1-(2,4,7-trimethyl)indenyl zirconium dichloride, dimethylsilylene (9-fluorenyl)-1-(2,4-dimethyl)indenyl zirconium dichloride or dimethylsilylene (9-fluorenyl)-1-(4,7-dimethyl)indenyl zirconium dichloride.

3. Process for producing novel metallocenes according to claim 1 comprising the following steps:

a) reacting dichloro-dialkyl(or diaryl)silane with (substituted indenyl)lithium to produce (substituted indenyl)-dialkyl(or diaryl)-chlorosilane, b) reacting said chlorosilane with fluorenyllithium to produce the (9-fluorenyl)-1-(substituted indenyl)-dialkyl(or diaryl)-silane precursor, c) reacting said (9-fluorenyl)-1-(substituted indenyl)-dialkyl(or diaryl)-silane precursor with butyllithium to produce its dilithium salt, and d) reacting said dilithium salt with zirconium chloride to produce the metallocenes.

4. Process for the polymerization of propylene to produce isotactic polypropylene, under propylene polymerization conditions, in the presence of a catalyst comprising a metallocene according to claim 1.

5. Process according to claim 4, wherein the metallocene is dimethylsilylene (9-fluorenyl)-1-(2,4,7-trimethyl)indenyl zirconium dichloride or dimethylsilylene (9-fluorenyl)-1-(2,4-dimethyl)indenyl zirconium dichloride.

* * * * *